United States Patent
Aberg et al.

(10) Patent No.: US 8,765,787 B2
(45) Date of Patent: *Jul. 1, 2014

(54) METHODS OF TREATMENT OF XEROPHTHALMIA WITH SELF-PRESERVING OCULAR FORMULATIONS OF NORKETOTIFEN

(75) Inventors: A.K. Gunnar Aberg, Sarasota, FL (US); Keith Johnson, Durham, NC (US)

(73) Assignee: Bridge Pharma, Inc., Sarasota, FL (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/622,509

(22) Filed: Nov. 20, 2009

(65) Prior Publication Data

US 2010/0130550 A1 May 27, 2010

(60) Provisional application No. 61/199,883, filed on Nov. 21, 2008.

(51) Int. Cl.
    *A61K 31/4535* (2006.01)
(52) U.S. Cl.
    USPC .......................................... 514/324; 514/912
(58) Field of Classification Search
    USPC ................................................ 514/324, 912
    See application file for complete search history.

(56) References Cited

U.S. PATENT DOCUMENTS

| | | | |
|---|---|---|---|
| 4,844,902 A | 7/1989 | Grohe | 424/449 |
| 5,369,095 A | 11/1994 | Kee et al. | 514/24 |
| 5,624,893 A | 4/1997 | Yanni | 514/21 |
| 5,776,445 A | 7/1998 | Cohen et al. | 424/78.04 |
| 5,939,426 A | 8/1999 | McCullough | |
| 6,207,684 B1 | 3/2001 | Aberg | 514/324 |
| 6,455,547 B1 | 9/2002 | Kis | 514/324 |
| 6,776,982 B2 | 8/2004 | Kis et al. | 424/78.04 |
| 7,226,934 B1 | 6/2007 | Aberg et al. | 514/324 |
| 7,247,623 B2 | 7/2007 | Yerxa et al. | |
| 7,270,830 B2 | 9/2007 | Reidenberg et al. | |
| 7,557,128 B2 | 7/2009 | Aberg et al. | 514/324 |
| 2002/0037883 A1 | 3/2002 | Singh | 514/171 |
| 2006/0148899 A1 | 7/2006 | Green et al. | |
| 2007/0014797 A1 | 1/2007 | Hitraya | |
| 2007/0112026 A1 | 5/2007 | Nagamoto et al. | |
| 2008/0085263 A1 | 4/2008 | Thuresson et al. | |
| 2008/0139531 A1 | 6/2008 | Yanni et al. | 514/214.02 |
| 2009/0269369 A1 | 10/2009 | Doi et al. | |
| 2009/0286718 A1 | 11/2009 | Stringer | |
| 2010/0105734 A1 | 4/2010 | Aberg et al. | |
| 2010/0130550 A1 | 5/2010 | Aberg et al. | |

FOREIGN PATENT DOCUMENTS

WO    2005/000307 A1    1/2005

OTHER PUBLICATIONS

Final Rejection mailed Feb. 17, 2012 in co-pending U.S. Appl. No. 12/317,575.
The International Search Report/Written Opinion dated Jan. 13, 2010.
Acta Ophthalmol. 2008: 86: 716-726; Christophe Baudouin; "Detrimental effect of preservatives in eyedrops: implications for the treatment of glaucoma".
Investigative Ophthalmology & Visual Science / Dec. 1983, vol. 24, 1624-1626; William J. Benjamin et al.; "Human Tears; Osmotic Characteristics".
Optometry and Vision Science; vol. 72, No. 10, pp. 713-717; J.P. Craig et al.; "Effect of Age on Tear Osmolality".
J Pharm Exptl Therap. 1944, 82: 377-390; John H. Draize et al.; "Methods for the study of irritation and toxicity of substances applied topically to the skin and mucous membranes".
Handbook of Ocular Disease Management—Chemical Burns; Dr. Wright Productions; Free Science; www.revoptom.com/handbook/sect3h.htm.
Chem. Pharm. Bull. 54(11) 1500-1507 (2006); Hongyi Qi et al.; "Optimization and Physicochemical Characterization of Thermosensitive Poloxamer Gel Containing Puerarin for Ophthalmic Use".
J Soc Cosmet Chem. 1962, 13:281-289; John H. Kay et al.; "Interpretation of eye irritation tests".
Research and Clinical Forums, 1982; 4:17-20; G.R. Kennedy; "Metabolism and pharmacokinetics of Ketotifen in children".
U.S. Pharmacopeia Convention, 2000: 1809; "(51) Antimicrobial Effectiveness Testing".
United States Pharmacopeia Excipient Verification Program; NF21, 2003—p. 21, 33, 74.
United States Pharmacopeia Excipient Drug Substance Verification Prorgram; p. 1, 29.
Helvetica Chimica Acta—vol. 59, Fasc. 3 (1976)—Nr. 87-88; pp. 866-877; E. Waldvogel et al.; "Untersuchungen uber synthetische Arzneimittel 9- und 10-Oxo-Derivate von 9, 10-Dihydro-4H-benzo[4,5] cyclohepta-[1,2-b] thiophenen".
Conjunctivitis—Wikipedia, Oct. 24, 2009.
Keratitis—Wikipedia, Sep. 18, 2009.
Progress in Retinal and Eye Research, vol. 29, 2010, pp. 312-334, "Preservatives in eyedrops: The good, the bad, and the ugly", Baudouin, et al.
Graefe's Arch Clin Exp Ophthalmol, vol. 241, 2003, pp. 1037-1043, "In vitro effects of preserved and unpreserved antiglaucoma drugs on apoptotic marker expression by human trabecular cells", Hamard, et al.
European Medicines Agency, EMEA Public Statement on Antimicrobial Preservatives in Ophthalmic Preparations for Human Use, Dec. 8, 2009, 1 page.
Office Action mailed Feb. 19, 2013 in co-pending U.S. Appl. No. 12/317,575.
Acta Ophthalmol. 2008: 86: 716-726, "Detrimental effect of preservatives in eyedrops: implications for the treatment of glaucoma", Baudouin.
Rapid Communications in Mass Spectrometry, 2003, vol. 17, pp. 2459-2463, "Determination of ketotifen and its conjugated metabolite in human plasma by liquid chromatography/tandem mass spectrometry: application to a pharmacokinetic study", Chen, et al.
Keratoconjunctivitis Sicca; The Merck Manual, 18th Edition; Corneal Disorders; pp. 899-900; (2006).

(Continued)

*Primary Examiner* — Zohreh Fay
(74) *Attorney, Agent, or Firm* — Cantor Colburn LLP

(57) ABSTRACT

Self-preserving ophthalmic formulations containing norketotifen and methods of making the same and the use thereof in patients suffering from xerophthalmia are disclosed. The methods also comprise administering to the eyes of a mammal in need thereof, self-preserving topical ophthalmic formulations containing norketotifen, free from any added preservative.

9 Claims, No Drawings

(56) References Cited

OTHER PUBLICATIONS

Gardner, Susanne; "What About the BAK?"; Advanced Ocular Care; May/Jun. 2011, pp. 31-33; (2011).

Notification and International Preliminary Report/Written Opinion on Patentability dated Jun. 3, 2011 in corresponding foreign patent application PCT/US2009/065252.

Handbook of Ocular Disease Management, 2009, http://www.revoptom.com/handbook/sect3h.htm, 1 page, "Chemical Burns", Dr. Wright Productions.

International Preliminary Examination Report dated Oct. 28, 2010 in co-pending PCT patent application No. PCT/US2008/14056.

Drugs.com, "Emadine", Feb. 2006, 3 pages, http://www.drugs.com/protemadine.html?printable=1.

Curr. Med. Res. Opin., Sep. 3, 2003, 19(4): 313-320, "Comparison of the Efficacy and Tolerability of Topically Administered Azelstine, Sodium Cromoglycate and Placebo in the Treatment of Seasonal Allergic Conjunctivitis and Rhino-Conjunctivitis", James, et al.

Life Sciences, 1987, vol. 40, No. 9, pp. 883-890, Species Differences in Metabolism of Ketotifen in Rat, Rabbit and Man: Demonstration of Similar Pathways In Vivo and in Cultured Hepatocytes:, Le Bigot, et al.

Daily Med: About DailyMed: "Patanol", Nov. 2007, 2 pages, http://dailymed.nlm.nih.gov/dailymed/drugInfo.cfm?id=5993.

Albrecht v. Graefes Arch. klin. exp. Ophthal. 192, pp. 141-150 (1974), 1 pg. summary, "Tear Volume in Normal Eyes and Keratoconjunctivitis sicca", Scherz, et al.

Eye & Contact Lens: Science & Clinical Practice: Dec. 2006, vol. 32, Iss. 6, pp. 272-276, 1 page Abstract, "Effect of Topical Ophthalmic Epinastine and Olopatadine on Tear Volume in Mice", Villareal, et al.

Novartis, "Zaditor", packet insert, Oct. 2002, 16137-E, 4 pages.

The CLAO Journal, Oct. 1995, vol. 21, No. 4, pp. 221-232. "Report of the National Eye Institute/Industry Workshop on Clinical Trials in Dry Eyes", Lemp, et al.

Alcon, Systane Lubricant Eye Drops, "Dry Eye Information; Tear Film Break-Up Time", 2008, 2 pages, http://www.systane.com/eyecare-professional/Tear-Film-Break-Up-Time.asp.

Br. J. Ophthalmol. 2002; 86: 181-184, Clinical Science, "Long term treatment with sodium hyaluronate-containing artificial tears reduces ocular surface damage in patients with dry eye", Aragona, et al.

Association for Research in Vision & Ophthalmology (ARVO), 2008 Annual Meeting, 1 page Abstract, #6316, "Assessment of Antimuscarinic Activity of Topical and Oral Antihistamines", Boyer, et al.

Review of Optometry, Special Edition, Sep. 2007: 48-52, Therapeutic Review, "Contact Lens-Related Dry Eye: Treatment tips for a common condition", Bowling.

Survey of Ophthalmology, 2001, vol. 45, Sup 2, 45 pages, S199-S202, Cat.Inist, 1 page Abstract, "Dry Eye Disease: The Scale of the Problem", Horst, et al.

CibaVision, "Zaditor: ketotifen fumarate ophthalmic solution, 0.025%", packet insert, 2002, 3 pages, Information to Patients.

Eye, 2000, 14: 892-898, 1 page Abstract, "Improvement of the ocular surface using hypotonic 0.4% hyaluronic acid drops in keratoconjunctivitis sicca", Iester, et al.

Am. J. Manag. Care, Apr. 2008, 14 (3 Suppl): S88-101, 1 page, "Management of Dry Eye Disease", PubMed result, Lemp.

Curr. Med. Res. Opin. 20(8): 1167-1173, 2004, Medscape, "Efficacy and Comfort of Olopatadine Versus Ketotifen Ophthalmic Solutions: A Double-Masked, Environmental Study of Patient Preference", http://www.medscape.com/viewarticle/489382_print, Leonardi, et al.

Arch. Ophthalmol., vol. 118, Sep. 2000, pp. 1264-1268, Epidemiology and Biostatistics, "Prevalence of and Risk Factors for Dry Eye Syndrome", Moss.

The Merck Manual of Diagnosis and Therapy, 2006, Corneal Disorders, "Keratoconjunctivitis Sicca", pp. 199-200, Beers, et al.

Ophthalmology Management, Sep. 2006, Supplement, 3 pages, http://www.ophmanagement.com/article.aspx?article=86656, "Understanding the Impact of BAK on Glaucoma Patients", Noecker, et al.

Agents Actions, Apr. 1988, 23 (3-4): 173-176, 1 pg. abstract, Pub Med Result, "Inhibition of basophil histamine release by methotrexate", http://www.ncbi.nlm.nih.gov/pubmed/2455981, Nolte, et al.

Clin. Ther., Apr. 2007, 29(4): 611-616, 1 page abstract, "An open-label, investigator-masked, crossover study of the ocular drying effects of two antihistamines, topical epinastine and systemaic loratadine, in adult volunteers with seasonal allergic conjunctivitis", Ousler, et al.

Alcon Laboratories, "Patanol (olopatadine hydrochloride ophthalmic solution 0.1%)", 1 page package insert, Jan. 2007.

Current Medical Research and Opinion, vol. 21, No. 9, Sep. 2005, pp. 1377-1388 (12), 1 page abstract, "Mast cell stabilization and antihistamine effects of olopatadine ophthalmic solution: a review of pre-clinical and clinical research", Rosenwasser, et al.

Eye Facts, University of Illinois, "Allergic Conjunctivitis", 3 pages, Jul. 1, 1990, http://www.uic.edu/com/eye/LearningAboutVision/EyeFacts/AllergicConjunctivitis.shtml.

Wikipedia, Oct. 2008, "Keratoconjunctivitis sicca", 8 pages, http://en.wikipedia.org/wiki/Keratoconjunctivitis_sicca.

XXVI European Academy of Allergology and Clinical Immunology (EAACI) Congress, Jun. 2007, 1 page, Evaluation of Muscarinic Receptor Antagonism by Antihistamines, Wolff, et al.

International Search Report and Written Opinion mailed Mar. 4, 2009 in co-pending PCT Patent Application No. PCT/US2008/14056.

Office Action dated Apr. 2, 2010 in co-pending U.S. Appl. No. 12/317,575.

Office Action dated Aug. 13, 2010 in co-pending U.S. Appl. No. 12/317,575.

Final Rejection dated Feb. 8, 2011 in co-pending U.S. Appl. No. 12/317,575.

Office Action dated Jul. 14, 2011 in co-pending U.S. Appl. No. 12/317,575.

Office Action mailed Aug. 28, 2012 in co-pending U.S. Appl. No. 12/317,575.

METHODS OF TREATMENT OF XEROPHTHALMIA WITH SELF-PRESERVING OCULAR FORMULATIONS OF NORKETOTIFEN

This application claims priority of Provisional Application Ser. No. 61/199,883, filed Nov. 21, 2008, the disclosure of which is hereby incorporated by reference.

FIELD OF THE INVENTION

The present invention relates to compositions for administration of the compound RS-norketotifen, hereinafter called norketotifen. This compound is useful for treating a variety of ocular disorders, including xerophthalmia and various forms of conjunctivitis and keratitis (U.S. Pat. No. 6,207,684).

Chemically, norketotifen is 4-(4-piperidyliden)-9-oxo-9,10-dihydro-4H-benzo[4,5]cyclohepta[1,2-b]thiophene, which is a mixture of R-norketotifen and S-norketotifen.

A large number of excipients have now been tested for compatibility with norketotifen and certain excipients have now been found to be compatible with norketotifen. Examples of compatible and incompatible excipients, such as for example members of the classes Antioxidants, Buffers, Chelating agents, Emollients, Gelling agents, Humectants, Mucoadhesive agents, Preservatives, Solvents, Stabilizers, Surfactants, Tonicity modifying agents and Viscosity modifying agents, have been identified and are described herein. Numerous compositions using said excipients have been prepared and tested.

The terms "composition" and "formulation" are used as synonyms herein. The terms "about" and "approximately" are used as synonyms herein. The terms "disorder" and "disease" are used as synonyms herein. The terms "carrier" and "solvent" are used as synonyms herein. The terms "norketotifen" and "norketotifen HF" as used herein refer to the hydrogen fumarate salt of said compound. The free base of norketotifen is herein called "norketotifen free base" or "norketotifen FB". As used herein, "about" means within the pharmaceutically acceptable limits found in the United States Pharmacopeia (USP-NF 21), 2003, or available at www.usp.org for amount of pharmaceutical ingredients.

BACKGROUND OF THE INVENTION

Embodiments disclosed herein relate to compositions of norketotifen that are intended for the treatment of ocular disorders, such as xerophthalmic disorders, allergic disorders and inflammatory disorders as well as combinations thereof, and methods of treating ocular disorders by administration of such compositions. The term "xerophthalmia" as used herein refers to conditions that are also called xerophthalmic disorders, keratoconjunctivitis sicca, keratitis sicca, sicca syndrome, dry eye syndrome, or dry eyes. The present invention also relates to formulations of norketotifen that are intended for the treatment of allergic (atopic) ocular diseases, such as for example allergic conjunctivitis and various other types of ocular inflammatory diseases, such as for example keratitis, keratoconjunctivitis, non-allergic conjunctivitis and various forms of blepharitis (inflammation of the eyelids).

Norketotifen is an active metabolite of ketotifen (Zaditor®, Novartis), which is used as an ocular medication for allergic disorders. Norketotifen has antihistaminic activity (Kennedy G R, 1982) that is about half of that of ketotifen when tested in vivo (Example 12.) Norketotifen is about ten times more active than ketotifen as anti-inflammatory compound (Example 13.)

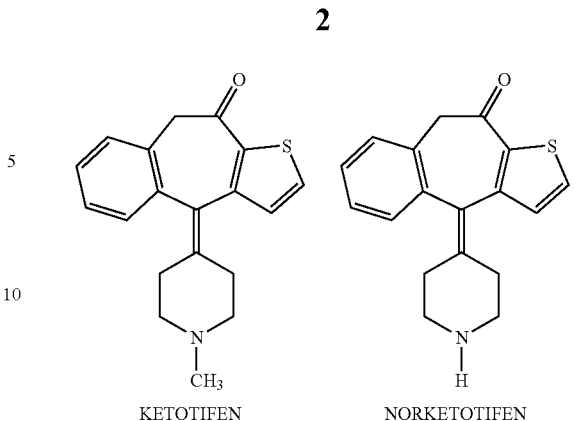

KETOTIFEN          NORKETOTIFEN

Ketotifen is available commercially, for example from Sigma-Aldrich (Internet: Sigma-Aldrich.com/order). Norketotifen can be made by demethylation of ketotifen according to the method described by Waldvogel et al. 1976, which publication is hereby incorporated by reference. However, this use of norketotifen is limited by its inherent irritability, as well as the irritability of certain excipients that were previously thought necessary to formulate an effective medicament, taking into account various issues including the limited solubility of the active ingredient norketotifen.

As described in U.S. Pat. No. 6,207,684, racemic norketotifen is useful for the treatment of various ocular conditions, such as for example conjunctivitis and keratitis. Further descriptions concerning S-norketotifen and R-norketotifen were presented in U.S. Pat. Nos. 7,226,934 and 7,557,128, respectively. Said patents are hereby incorporated by reference. It has now been found that selected formulations of norketotifen are well tolerated by mammalian ocular tissues and have the surprising effect of decreasing or eliminating the ocular irritating activity of norketotifen when applied to the eye. Said selected formulations (herein called "preferred formulations") of norketotifen are suitable for daily topical administrations. Ocular administration of ophthalmic medication is the preferred route of administration.

Due to its physicochemical properties and its pharmacological effects, such as low anti-muscarinic activity, norketotifen is well suited for ocular use.

To our knowledge, methods of administering norketotifen in a preferred formulation topically to the eye or into the conjunctival sac of patients suffering from eye disorders have not previously been described. The therapeutic use of selected ocular formulations containing norketotifen has not been described, as formulations for the ocular administration of norketotifen have previously not been developed. Ocular formulations of ketotifen have been described (U.S. Pat. No. 6,455,547) but are of no relevance for norketotifen since the physicochemical properties for norketotifen HF are vastly different from those of ketotifen—as an example, the water solubility for ketotifen is about 12.5 mg/ml and the water solubility of norketotifen is about 2.16 mg/ml.

Although hundreds of ophthalmic excipients exist, it is far from obvious what excipients may be compatible with norketotifen and what combinations of excipients and what concentrations thereof should be used to obtain optimal ophthalmic compositions that may optimize that ocular therapeutic activities and decrease the ocular side effects of norketotifen. This may be due to the fact that norketotifen has physicochemical, chemical and pharmacological properties and side effects that are unique to this specific molecule and therefore, new compositions have to be developed for norketotifen. It is a well-known fact that for example all the different ocular steroids need different ophthalmic formulations (compositions). Each composition is depending on the physicochemical and the pharmacological properties of the active molecule(s) and the therapeutic effects sought. In the case of norketotifen, our research has now arrived at compositions that are acceptable to the patients, therapeutically efficacious, allowing for once-daily ocular administration or for repeated daily ocular administrations to mammals in need thereof, while decreasing or even inhibiting certain ocular side effects of norketotifen. Selected ocular compositions have now been found, which offer pharmaceutical compatibility between the active ingredient and the excipients, optimize the therapeutic activities of norketotifen and decrease the ocular side effects thereof.

The preferred formulations of the present invention, as described herein are chemically stable and commercially feasible to manufacture.

It is an objective of the present invention to provide ocular compositions that deliver therapeutically effective concentrations of norketotifen to the eye and the conjunctival tissues, which allow for once-daily ocular administration or for repeated ocular administrations from two to five times daily to a mammal in need thereof, while not causing ocular side effects, such as burning, redness or irritation, and while at the same time being stable upon storage. The terms "therapeutically effective (dose)" and "therapeutically efficacious (dose)" refer to a dose that yields therapeutic benefit to patients, which in the present case refers to therapeutic benefit to patients suffering from allergic and/or inflammatory condition(s).

The present invention may be useful for patients in need of medication for ocular inflammatory and ocular allergic disorders and for patients suffering from xerophthalmic disorders. The term "patients" in this document refers to mammals, such as for example humans, dogs and cats. Preferred are human patients.

Patients suffering from ocular allergic and/or inflammatory disorders include individuals being diagnosed as suffering, for example, from various types of conjunctivitis, as for example allergic conjunctivitis, seasonal allergic conjunctivitis, chronic allergic conjunctivitis, atopic keratoconjunctivitis or vernal conjunctivitis. As used herein, the term "conjunctivitis" refers to all forms of the disease. These patients often have symptoms, such as for example hyperemia of the bulbar conjunctiva, discharge, limbal erythema/swelling or erythema/swelling of the eyelids, itching, decreased lacrimation, photophobia, discomfort, foreign body sensation and/or xerophthalmia.

Keratitis is a condition in which the eye's cornea becomes inflamed. Various forms of keratitis exist, such as for example superficial keratitis and deep keratitis. As used herein, the term "keratitis" refers to all forms of the disease.

The terms "dry eye disease" and "xerophthalmia" are used synonymously herein and refer to various disorders that are well known to those skilled in the art of ophthalmology. Examples of xerophthalmic disorders are keratoconjunctivitis sicca, age-related dry eye, Stevens-Johnson syndrome, Sjögren's syndrome, ocular cicatrical pemphigoid, blepharitis, corneal injury, infections, Riley-Day syndrome, congenital alacrima, nutritional disorders or deficiencies (including vitamin A deficiency), autoimmune and other immunodeficient disorder and side effects of medications such as for example anticholinergic drugs used for overactive bladder syndrome and urinary urge incontinence. As used herein, the term "dry eye disease" or "xerophthalmia" refer to all forms of the disease.

All compositions intended for use in the eye are required to be sterile, endotoxin-free and foreign particulate free. The term "foreign particulate free" indicates the absence of any particulate matter, but excludes drug particles, controlled release microparticulates and the like. Conventional methods for the manufacture of sterile compositions include sterilization by moist heat (autoclaving), sterilization by dry heat, ethylene oxide sterilization (gaseous sterilization), exposure to ultraviolet rays or to gamma irradiation or sterilization by aseptic processing or filtration through sterilizing grade filters.

Norketotifen formulations for ocular administration that are described herein can be readily processed by standard manufacturing processes, which are well known to those skilled in the art.

SUMMARY OF THE INVENTION

The physicochemical properties of norketotifen have now been investigated, with particular focus on the solubility and stability properties of the compound. The compatibility of norketotifen with a large number of ocular excipients has been studied. The optimal concentration range, acidity range and tonicity range for ocular formulations of norketotifen have been determined from the present studies. It was determined that the concentration of norketotifen in the compositions of the invention should be between 0.001 percent and 0.3 percent, preferably between 0.01 percent and 0.25 percent. Formulations containing one or more solubilizing excipient may contain norketotifen in concentrations from 0.001 percent to 5.0 percent, more preferred from 0.01 percent to 1.9 percent. The acidity of the final ocular composition should be between pH 4.0 to pH 6.5, preferably between pH 5.2 to pH 6.2. The tonicity of final aqueous ocular solutions should be from 150 mOsm to 450 mOsm and preferably from 230 mOsm to 330 mOsm.

Therapeutically effective ophthalmic compositions of norketotifen, containing excipients that are compatible with this drug have now been developed and formulations, such as ocular solutions, ocular hydrophilic ointments and gels, ocular hydrophobic ointments, ocular emulsions and ocular liposome formulations, all containing norketotifen, have now been developed and are described herein. It was an objective to develop formulations of norketotifen that allow for once-daily ocular administration and for repeated ocular administrations from two to five times daily to patients in need thereof.

"Therapeutically effective" ocular solution formulations of norketotifen refer to concentration of norketotifen from 0.001 percent to 0.30 percent; more preferred are concentrations from 0.01 percent to 0.25 percent by weight. "Therapeutically effective" formulations with one or more solubilizing excipient refer to norketotifen concentrations from 0.001 percent to 5.0 percent by weight, more preferred from 0.01 percent to 1.0 percent by weight.

An eyedropper device is usually used for the administration of ophthalmic solutions to the eye. The volume of each drop depends on the construction of the device, the technique used to produce the drop and the viscosity of the solution being administered. Commercial eyedroppers usually deliver drops with a volume of 50 µL. Thus one drop of norketotifen 0.1 percent equals an amount of 50 µg norketotifen.

A squeezable tube with a small tip is usually used for the administration of gels or ointments to the eye. The amount administered depends on the technique used and the design of the tube. The amount of the gel or ointment dosed is usually from about 20 mg to about 50 mg for each application.

During biological testing it was surprisingly found that the preferred formulations described herein completely protected the ocular tissues from irritation by norketotifen, even if the highest possible concentrations of norketotifen were used.

Microbiological testing, using standard preservative challenge tests, surprisingly demonstrated self-preservation qualities of the preferred norketotifen formulations. Thus, said formulations can be used without added preservatives.

DETAILED DESCRIPTION OF THE INVENTION

The term norketotifen as used herein relates to the basic compound itself as well to any pharmaceutically acceptable salt thereof. Preferred pharmaceutically acceptable salts of norketotifen are for example a hydrogen fumarate, a hydrochloride, a hydrobromide, a hydrogen maleate, or a hydrogen sulfate. More preferred salts of norketotifen are the hydrochloride salts and hydrogen fumarate salt. Most preferred is the hydrogen fumarate salt. The term "pharmaceutically acceptable salt" and the like refer to salts prepared from pharmaceutically acceptable acids, such as for example fumaric, hydrobromic, hydrochloric, maleic and sulphuric acids.

The term "therapeutically effective ocular formulations of norketotifen" refers to solutions containing norketotifen in concentrations from about 0.001 percent to about 0.30 percent; more preferred are concentrations from 0.01 percent to 0.250 percent. Formulations containing one or more excipient with solubilizing activity may contain higher concentrations of norketotifen than indicated above. Thus, for example gels, ointments and solutions containing solubilizing excipients may contain norketotifen in concentrations in excess of 5.0 percent. Therefore, "therapeutically effective" ocular formulations containing one or more solubilizing excipient contain norketotifen in concentrations from about 0.001 percent to about 5.0 percent, more preferred are concentrations from about 0.01 percent to about 1.0 percent.

The present invention provides pharmaceutical compositions, which comprise norketotifen formulated together with carefully selected excipients. The pharmaceutical compositions of the present inventions concern formulations of norketotifen that are intended for topical ophthalmic use by patients suffering from ocular disorders, such as allergic or inflammatory disorders or both allergic and inflammatory disorders. The terms "composition" and "formulation" are used as synonyms herein. If not stated to the contrary, all percent (%) concentrations in this document refer to percentage by weight (w/w).

The solubility of norketotifen has now been investigated in water and in formulations with various excipients. The water solubility of norketotifen is low but it was found that the solubility was not further decreased in the formulations of the present invention (Example 10).

The stability of norketotifen formulations has now been investigated. While some excipients significantly decreased the stability, the preferred formulations that are presented herein, have demonstrated acceptable stability (Example 11).

The therapeutically useful pH-range of solutions of norketotifen was limited by decreased chemical stability of norketotifen at pH ≥6.5 (Example 11). The lowest tolerated pH of ocular formulations is known to be about pH 4, since formulations with pH <4 may induce chemical burns (Dr Wright Productions, Handbook of Ocular Disease Management, 2009). Thus, the acidity of ocular formulations of norketotifen should be from pH 4 to pH 6.5, preferably from about pH 5.2 to about pH 6.2.

The tonicity of norketotifen formulations should be isotonic to human tears (Benjamin et al., 1983; and Craig e al., 1995.) or slightly hypotonic. It was therefore determined that the tonicity should be from about 150 mOsm to about 450 mOsm, preferably from about 230 mOsm to about 330 mOsm. As used herein, the term "mOsm" is a measurement of osmolality and refers to milliosmoles per kilogram of solvent.

The viscosity of norketotifen formulations should be within a range that feels comfortable to the patient, while not causing blurring of the vision. Furthermore, the norketotifen formulations should have a viscosity that can be handled easily during manufacturing and filling. It was determined that the norketotifen formulations of the present invention should have viscosity of about 1.0 to about 100,000 centipoise (cP), preferably between about 2.0 to about 90,000 cP and most preferably from about 2.5 to about 75,000 cP, when tested at room temperature. As used herein, the term "cP" indicates a measurement of viscosity and refers to centipoise (water has the viscosity of 1 centipoise at 20° C.). As used herein, the terms "compatible", "compatibility" and the like, relate to the compatibility between the excipient(s) and the active ingredient norketotifen.

All compositions intended for use in the eye are required to be sterile. The choice of an appropriate method for sterilization is within the scope of understanding of a person of ordinary skill in the art of manufacturing ocular dosage forms. Norketotifen compositions, of the present invention, which are stable to increased temperatures, can be sterilized by moist heat (autoclaving).

The term autoclaving relates to a standardized thermal heating procedure characterized by: Heating a test composition to 120° C. or more for a period of 15 minutes or more, wherein said composition is aqueous. Said aqueous composition is kept in a closed vessel, which vessel is typically a plastic or glass bottle. The pressure during autoclaving is typically 1 bar or more. The autoclaving may preferably range from 120 to 150° C., more preferably from 120 to 140° C.; the time needed may preferably range from 15 to 120 minutes, more preferably from 15 to 60 minutes; and the pressure applied may preferably range from 1 to 20 bar, more preferably from 1 to 10 bar, and even more preferably form 1 to 5 bar.

Alternatively, ocular norketotifen compositions can be exposure to ultraviolet rays or to irradiation, such as gamma irradiation. Formulations can also be processed aseptically, which includes filtration through sterilizing grade filters, which may have a nominal pore size of 0.22 μm.

Maintaining sterility in multiple-use containers is usually achieved by adding one or more preservatives to the formulations. Alternatively, sterilized single-unit dose packages, such as for example single unit dose vials, ampoules or syringes, containing a sterile norketotifen formulation, as described herein, may be used. However, the manufacturing, handling and distribution of single-unit dose packages are expensive and the use thereof may be complicated to the patient.

In an embodiment of the present invention, it has now been found that formulations containing norketotifen are self-preserving (Example 9). The term "self-preserving" as used herein means that said norketotifen formulations do not support microbial growth despite the absence of the addition of any conventional preservatives in the formulation. The term "formulations do not support microbial growth" means that the number of inoculated colonies in a formulation remain the same or decline in preservative challenge tests carried out on said formulation. A self-preserving formulation of norketotifen will not need a preservative, such as for example BAK, to be included as an excipient in said formulation. Accordingly, when used in the claims, the term "consisting essentially of" means that any ingredient that if present in the formulation, would be present in an amount effective to have a preservative effect on the formulation, is excluded.

Alternatively, the self-preserving effects of the present norketotifen formulations may allow the use of very low concentrations of preservative agents. A "very low concentration" of the preservative agent BAK is an amount corresponding to a concentration that is less than 0.001 percent by weight of said formulation. A "very low concentration" of the preservative agent PHMB is an amount corresponding to a concentration that is equal or less than 1 ppm. Surprisingly, it has now been found that the anti-microbial effect of norketotifen formulations is pH-dependent; self-preservation was observed in norketotifen formulations at pH 5.0 or higher.

In another embodiment of the present invention, it has now surprisingly been found that the preferred formulations of norketotifen prevent the expression of unwanted ocular effects of norketotifen or any excipient(s) being used. Thus, the preferred norketotifen formulations prevent or inhibit any unwanted effects on the cornea (such as for example the formation of opacities), on the iris (such as for example congestion, swelling or reaction to light) or on the conjunctivae (such as for example redness, swelling or discharge formation). It has now surprisingly been found that certain preferred formulations of norketotifen have the ability to completely prevent any and all ocular side effects of norketotifen even at the highest concentrations of norketotifen that can be prepared in ocular solutions.

In another embodiment, it has surprisingly been found that the preferred ocular formulations of norketotifen do not decrease the solubility of norketotifen, but actually increase said solubility. Thus, the solubility of norketotifen at pH 4.0 was found to be 2.16 mg/ml in water and the solubility remained approximately the same as pH was increased (by adding NaOH) to pH 5.0, 6.0 or 7.0. The solubility of norketotifen in buffered water was slightly decreased to 2.10 mg/ml at pH 8.6. The solubility of norketotifen was sharply decreased at higher pH and at pH 8.75 the solubility of norketotifen was decreased to approximately 1.0 mg/ml. In the preferred solution formulations NOBAK, LOBAK, MIDBAK, HIBAK, PHMB, S1008, S1009 and S1010 (Tables 1A and 1B), the solubility of norketotifen was about 2.4 mg/ml (pH 5.5). The solubility on norketotifen could be significantly increased is certain formulations, such as gels and ointments where solvents were not water. Thus, the solubility of norketotifen was about 10 mg/ml in propylene glycol.

To avoid ocular irritation by foreign particles, all formulations have to be foreign particulate free. The term "foreign particulate free" indicates the absence of any particulate matter, but excludes drug particles, controlled release microparticulates and the like.

Norketotifen compositions of the present invention can be filled into vials, ampoules, syringes or the like and then lyophilized. Lyophilized products, which are free from moisture, are then reconstituted before administration providing a prolonged shelf life.

The norketotifen formulations for ocular administration that are described herein can be readily processed by standard manufacturing processes, well known to those skilled in the art of manufacturing ocular dosage forms.

Excipients Compatible with Norketotifen

Suitable excipients, compatible with norketotifen, include specific antioxidants, buffers, chelating agents, emollients, emulsifiers, fillers, gelling agents, humectants, mucoadhesives, preservatives, solvents, stabilizers, surfactants, tonicity agents and viscosity modifying agents. It can be noted that one and the same excipient can belong to various classes; thus, for example edetate (EDTA) can have buffering activity, chelating activity, preservative activity, stabilizing activity (also during autoclaving procedures), viscosity modifying activity and possibly additional activities. Another example is propylene glycol that is used in formulation S1009 (Table 1B) as a solvent/moisturizer/tonicity modifier.

The term "EDTA", as used herein, comprises the chemical compound ethylenediaminetetraacetic acid and the disodium and calcium disodium salts thereof. EDTA and the salts thereof have many names, such as for example edetate, disodium edetate. ED3A (ethylenediaminetriacetic acid) may be used instead of or in addition to EDTA in the compositions described herein.

Antioxidants are compounds that act to slow or prevent the oxidation of other chemicals. Suitable antioxidants that are compatible with norketotifen include sulfites, ascorbates, acetylcystein, butylated hydroxyanisole (BHA) and butylated hydroxytoluene (BHT). When needed, compatible antioxidants can be used in all formulations mentioned herein. Useful concentrations range from about 0.05 percent to about 3 percent, preferably 0.1 percent to 0.25 percent, by weight.

Buffering agents are used to adjust the pH of a solution. The function of a buffering agent is to drive an acidic or alkaline solution to a certain pH range and prevent a change from this pH. Buffering agents have variable properties—some are more soluble than others; some are acidic while others are basic. Suitable buffering agents that are compatible with norketotifen include phosphates, boric acid, borates, citrates and acetates. Buffers will be used in the concentrations needed to stabilize the acidity between pH 4.6 and pH 6.5, preferably between pH 5.2 and pH 6.2. The amount of each of the buffering compounds needed may range from about 0.01 percent to about 4 percent by weight, preferably from 0.05 percent to 1 percent by weight. Ocular compositions with pH ≤4.0 are usually not well accepted by patients and ocular compositions of norketotifen with pH ≥6.5 have now been found to decrease long-term chemical stability. Thus, the acidity of ocular norketotifen compositions should be between about pH 4 and about pH 6.5, preferably between pH 5.2 and pH 6.2. When needed, compatible buffering agents can be used in all formulations mentioned herein. The acidity of all formulations described herein can be adjusted by changing the concentrations of the buffering agents or by adding an acid or a base as known to those skilled in the art.

Chelating agents, which are often organic compounds, are also called chelants, or sequestering agents and have the ability to form a chelate complex with a substrate. Known chelating agents are for example, edetate, proteins, polysaccharides, polynucleic acids and chelating polymers. Suitable chelating agents compatible with norketotifen are edetate and chitosan polysaccharides. If needed, chelating agents may be used in concentrations from about 0.01 percent to about 10 percent, preferably from 0.01 percent to 2.0 percent by weight. Some chelating agents, for example chitosan polysaccharides, also have mucoadhesive properties. When needed, compatible chelating agents can be used in all formulations mentioned herein.

Emollients cause occlusion of mucous membranes by providing a layer of oil to slow water loss from mucous membranes of the eye. Emollients also act as humectants and thereby improve the water-holding capacity of the ocular tissues. Emollients also act as lubricants, whereby these agents add slip or glide to the mucous membranes of the cornea and the conjunctival membranes. Emollients can be used in the ocular formulations of the present invention only if said emollients meet the criteria of being active at pH ≤6.0 and if they do not decrease the chemical stability of norketotifen. Suitable emollients compatible with norketotifen include, for example, glycerin, propylene glycol, and hypromellose (hydroxypropyl methylcellulose, HPMC). When needed, compatible emollients can be used in all formulations mentioned herein. If needed, said emollients can be used in concentrations from about 0.1 percent to about 10 percent and preferably in concentrations from 0.1 percent to 2 percent by weight in the norketotifen formulations described herein.

Gelling agents (viscosity-modifying agents) are used to thicken and stabilize liquid solutions, emulsions and suspensions, thereby inducing retention of the compositions in the ocular tear fluid. Gelling agents dissolve in solutions, giving an appearance of a more or less solid matter, while being mostly composed of a liquid. Examples of suitable gelling agents compatible with norketotifen include edetate (EDTA), alginic acid and alginates, carrageenan, pectin, gelatin and gelling polymers. When needed, compatible gelling agents can be used in all formulations mentioned herein. Gelling agents can be used in concentrations from about 0.05 percent to about 10 percent and preferably in concentrations from 0.1 to 2.5 percent by weight.

In situ gelling agents may be included in ocular formulations of norketotifen and are instilled as drops into the eye and undergo sol-to-gel transition in the tear fluid, due, for example, to ion-triggered activation, pH-triggered activation or thermal activation. Examples: Alginate is a gelling agent that can be used in combination with the viscosity-enhancing agent hydroxypropyl methylcellulose (HPMC). The rheological behavior of the alginate/HPMC solutions were retained in the presence of norketotifen and was found to be a useful ion-activated in situ gelling system for norketotifen-containing compositions. Polyacrylic acid (Carbopol) is a gelling agent in combination with the viscosity-enhancing agent hydroxypropyl methylcellulose (HPMC) and is a useful pH-triggered in situ gelling system for norketotifen-containing compositions. Poloxamer 407 is a polymer with a solution viscosity that increases when its temperature is raised to the eye temperature (Hongyi et al. 2006). The temperature-sensitive rheological behavior of Poloxamer 407 or Poloxamer 407/188 mixtures was not influenced by the presence of norketotifen. Suitable in situ gelling agents compatible with norketotifen were also found to include alginate/hydroxypropyl methylcellulose, polyacrylic acid/hydroxypropyl methylcellulose. In situ gelling agents as described above can be used in concentrations from about 0.5 percent to about 10 percent, preferably from 0.1 percent to 2.5 percent by weight. Poloxamers can be used in higher concentrations, up to 25 percent by weight.

Humectants can be used to soften biological tissues as they increase the water-holding capacity of ocular tissues, such as the cornea and the conjunctival membranes and certain humectants were found to be compatible with norketotifen and can be used in ocular formulations of norketotifen. Suitable humectants that are found to be compatible with norketotifen include polyethylene glycol, sorbitol and propylene glycol. When needed, compatible humectants can be used in all formulations mentioned herein. Said humectants are used in concentrations from about 0.05 percent to about 10 percent, preferably from 0.1 percent to less than 4 percent and more preferably from 0.1 percent to 2 percent by weight.

Lubricants can hold moisture on the eye. Numerous polymers can be used as ocular lubricants. Suitable lubricants that are compatible with norketotifen include methylcellulose, hydroxypropylmethylcellulose, hydroxyethylcellulose, thiolated acrylic acid polymers, carbomer, carboxymethylcellulose sodium, chitosans, and polyisobutylcyanoacrylate. When needed, compatible lubricants can be used in all formulations mentioned herein. If needed, the concentrations of said lubricant is from 0.1 percent to 10 percent, preferably from about 0.1 percent to about 4 percent and more preferably from 0.1 percent to 2 percent by weight.

Mucoadhesive agents refer to materials that will adhere to mucus and mucosal membranes. Suitable mucoadhesives that are compatible with norketotifen formulations described here include thiolated acrylic acid polymers, chitosan, polyisobutylcyanoacrylate and ethylcellulose. Mucoadhesive polymers, such as mucoadhesive chitosan and mucoadhesive chitosan-coated microspheres or liposomes will be useful for prolonged delivery of norketotifen to the eye. Mucoadhesive agents can be used in concentrations from about 0.1 percent to about 10 percent, preferably from 0.1 to 2 percent by weight. If needed, compatible mucoadhesive agents can be used in all formulations mentioned herein.

Using compatible mucoadhesive agents, norketotifen can be administered to patients as ocular mucoadhesive minitablets, microspheres and as ocular gel-forming minitablets (see Example 7 below).

Preservatives are substances that can be used to prevent the growth of microorganisms in ophthalmic formulations. Suitable preservatives that are compatible with norketotifen include stabilized oxychloro complexes, benzalkonium chloride (BAK), polyhexamethylene biguanide (PHMB). Sorbic acid was found to be incompatible with norketotifen since this preservative decreased the stability of norketotifen solutions. A suitable concentration of a stabilized oxychloro complex is from 0.003 percent to 0.01 percent by weight and a suitable concentration of BAK is from 0.0001 percent (1 ppm) to 0.05 percent (500 ppm) preferably 0.0001 percent to 0.02 percent by weight. A suitable concentration of PHMB is from 0.00001 percent (0.1 ppm) to 0.005 percent (50 ppm), preferably from 0.0005 percent (5 ppm) to 0.00005 percent (0.5 ppm). Any preservative mentioned here may be combined with one or more other preservatives for improved efficacy. The concentrations of preservatives may be kept lower than shown here, including the case where no preservatives are used, since formulations containing norketotifen have now been found to be self-preserving.

In addition to water, which is the preferred carrier, other solvents like polyethylene glycol (PEG) and/or propylene glycol (PG) can be used in ophthalmic compositions. Norketotifen HF was found to be soluble in a polyethylene glycol (PEG 300) up to 0.15 percent w/w. Propylene glycol can be used as a solvent to obtain high concentrations of norketotifen in ophthalmic ointments and gels since norketotifen HF, has now, surprisingly, been found to be soluble in propylene glycol up to 1.0 percent by weight. Norketotifen can be dissolved in water in concentrations up to 0.216 percent by weight. Suitable non-aqueous solvents include polyethylene glycol (about 0.1 percent to about 90 percent) and propylene glycol (about 0.1 percent to about 90 percent). Both BAK and PHMB were compatible with norketotifen and can be used in all formulations mentioned herein.

Stabilizers in ophthalmic formulations enhance the physical stability of ocular compositions, such as for example emulsions. It was found that several known stabilizers, such as for example xanthan gum and carbomers (acrylic acid polymers), were not compatible with norketotifen since hazy suspensions were formed. Suitable stabilizers that are compatible with norketotifen include methylcellulose, edetate, chitosan, hydroxypropylmethylcellulose and hydroxyethylcellulose. Terms, such as "stabilization", "stabilizer", "stability", when used herein relate to the stability of the pharmaceutical formulation in total and in particular to the stability of norketotifen when exposed to storage, oxygen, air, light and or heat (including high-temperature sterilization, such as autoclavation). The compatible stabilizers listed here are usually used in concentrations from about 0.05 percent to about 4 percent and preferably from 0.05 percent to 2 percent by weight.

Combined stabilizer/solubilizers may be used in formulations containing norketotifen. Such combined additional stabilizer/solubilizers are for example cyclodextrins. A preferred cyclodextrin is in particular selected from the group of (α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin. The concentrations are generally in the range of from about 0.01 percent to about 90 percent, more preferably in the range of from about 0.1 to about 20 percent by weight.

Surfactants reduce the surface tension of liquids, such as for example water. Suitable surfactants that are compatible with norketotifen include nonionic surfactants, such as for example polysorbates, glyceryl stearate, lecithins, polyethoxylated castor oil derivatives and oxyethylated tertiary octylphenol formaldehyde polymers, which in combinations with norketotifen were all found to be less irritating to the eye than ionic surfactants, which may also be used. If needed, compatible surfactants can be used in all formulations mentioned herein. Surfactants are usually used in concentrations from about 0.05 percent to about 4 percent and preferably from 0.1 percent to 2 percent by weight.

Tonicity-adjusting agents increase the effective osmolarity or effective osmolality of a formulation. Hypertonic, hypotonic and isotonic solutions are defined in reference to a cell membrane by comparing the tonicity of the solution with the tonicity within the cell. Ocular compositions preferably contain a tonicity-adjusting agent in an amount sufficient to cause the final composition to have an ophthalmically acceptable osmolality (generally 150 to 450 mOsm and preferably 230 to 330 mOsm). Suitable tonicity-adjusting agents to be used with norketotifen may be of ionic and/or non-ionic type. An example of ionic type tonicity enhancers is sodium chloride and examples of non-ionic tonicity enhancing agents are, for example sorbitol and propylene glycol, which are compatible with norketotifen. Thus, norketotifen formulations may include for example sodium chloride in concentrations from about 0.1 to about 0.9 percent by weight, sorbitol in concentrations from about 0.1 to about 10 percent or propylene glycol in concentrations from about 0.1 to about 10 percent by weight. If needed, compatible tonicity-adjusting agents can be used in all formulations mentioned herein. All ophthalmic formulations of norketotifen were adjusted to be approximately iso-osmotic to human tears (Benjamin et al., 1983; Craig et al., 1995.)

Viscosity-adjusting agents increase the internal friction ("thickness") of a formulation. The ophthalmic solutions of the present invention may contain one or more viscosity-adjusting agent and have a viscosity of 1.0 to 100,000 cP, preferably between 2.0 to 90,000 cP, and most preferred between 2.5 and 75,000 cP, which is acceptable since compositions in this range of viscosity feel comfortable to the eye and do not cause blurring of the vision. Viscosity modifying agents can be used in ophthalmic compositions and are substances that have the ability to cause thickening (increase the viscosity) of ophthalmic formulations. Viscosified solutions are accepted to a great degree by patients, mainly because of the ease of administration. Some viscosity modifying agents, such as for example xanthan gum, were not compatible with norketotifen. Viscosity modifying agents that are compatible with norketotifen include edetate, methylcellulose, carboxymethylcellulose, hydroxypropyl methylcellulose, hydroxyethyl cellulose, polyethylene glycol, propylene glycol alginate, chitosan, and tragacanth. The term "hydrogels" is often used for viscosity enhancing excipients, particularly in artificial tears and refers to a colloid with high gelling ability. If needed, compatible viscosity-adjusting agents can be used in all formulations mentioned herein. When needed, the concentrations of the selected viscosity modifying agents range from about 0.1 percent to about 10 percent by weight, and preferably between 1 percent and 5 percent. Sorbitol may be used as a combined tonicity-adjusting and viscosity-adjusting excipient in a concentration range from about 0.1 to about 10 percent, preferably from 2 percent to 5 percent.

There are currently two strategies to increase the retention time of ocular formulations in the eye. Thus, either excipients can be used that have bioadhesive properties, such as for example mucoadhesive excipients, or the formulation can be made more viscous. Both strategies are included in the present invention.

In certain embodiments, the compositions containing norketotifen are packed in opaque plastic containers that may be sterilized using for example ethylene oxide or gamma radiation. A preferred container for an ophthalmic product may be equipped with an eyedropper. Single-dose containers may be used and have advantages that are obvious to those skilled in the art.

Compositions Compatible with Norketotifen

Using excipients that had been found to be compatible with norketotifen, compositions such as topical ophthalmic solutions, topical ophthalmic gels, topical hydrophilic ophthalmic ointments, topical ophthalmic emulsions, and topical ophthalmic liposome compositions were prepared as demonstrated in the following Examples. The prepared formulations were tested for physical appearance and stability (refrigerated, room temperature, and at increased temperatures) using analytical methodology as described in Example 10.

EXAMPLES

Certain embodiments of the present invention are illustrated in the following examples. The embodiments described in this specification are considered to be illustrative in all respects and not restrictive. The scope of this invention is indicated by the appended claims, not by this description.

An HPLC method for the determination of concentrations of norketotifen was developed (Example 10). The excipients used in the present compositions can be analyzed using standard methods that are well known to those skilled in the art.

Example 1

Ophthalmic Solutions

Examples of preferred solution formulations containing norketotifen hydrogen fumarate are shown in Tables 1A and 1B.

Preferred solution formulations containing norketotifen may contain excipients at different concentrations from those shown in Tables 1A and 1B.

Other useful solution formulation containing norketotifen may contain excipients that are different from those shown in Tables 1A and 1B.

TABLE 1A

Examples of preferred solution formulations containing norketotifen HF.

| Excipients in % | NOBAK | LOBAK | MIDBAK | HIBAK | PHMB |
|---|---|---|---|---|---|
| Norketotifen HF (*) (%) | 0.0345 (1) | 0.0345 (1) | 0.0345 (1) | 0.0345 (1) | 0.0345 (1) |
| EDTA | 0.100 | 0.100 | 0.100 | 0.100 | 0.100 |
| Boric Acid | 0.095 | 0.095 | 0.095 | 0.095 | 0.095 |
| BAK | — | ≤0.001 (**) | 0.005 | 0.010 | — |
| PHMB | — | — | — | — | 0.0001 |
| Sorbitol | 4.600 | 4.600 | 4.600 | 4.600 | 4.600 |
| Water | q.s. | q.s. | q.s. | q.s. | q.s. |
| pH (***) | 4.6-6.2 | 4.6-6.2 | 4.6-6.2 | 4.6-6.2 | 4.6-6.2 |

(1) Norketotifen HF 0.0345 percent is equivalent to norketotifen FB 0.025 percent.
(*) Norketotifen may be used in concentrations from 0.01 to 0.3 percent.
(**) BAK-concentration is from 0.0001% to 0.001%, preferably 0.0005%
(***) pH is between 4.6 and 6.2, preferably 5.5.

TABLE 1B

Examples of preferred solution formulations containing norketotifen.

| Excipients in percent | S1008 | S1009 | S1010 |
|---|---|---|---|
| Norketotifen HF (%) (*) | 0.0345 (1) | 0.208 (2) | 0.208 (2) |
| Sodium phosphate dibasic | 0.473 | — | 0.160 |
| Sodium phosphate•monobasic, monohydrate | 0.460 | — | — |
| NaCl | 0.480 | — | — |
| BAK | 0.010 | — | 0.010 |
| Sodium citrate | — | 0.300 | — |
| Propylene glycol | — | 1.750 | — |
| Methylparaben | — | 0.030 | — |
| Propylparaben | — | 0.010 | — |
| Methylcellulose | — | — | 0.500 |
| Glycerin | — | — | 2.400 |
| Water | q.s. | q.s. | q.s. |
| pH (**) | 4.6-6.2 | 4.6-6.2 | 4.6-6.2 |

(1) Norketotifen HF 0.0345 percent is equivalent to 0.025 percent norketotifen FB.
(2) Norketotifen HF 0.208 percent is equivalent to 0.15 percent norketotifen FB.
(*) Norketotifen HF may be used in concentrations from 0.01% to 0.3%.
(**) pH is between 4.6 and 6.2, preferably adjusted to 5.5.

All ophthalmic formulations of norketotifen were adjusted to be approximately iso-osmotic to human tears (Benjamin et al., 1983; Craig et al., 1995.)

If needed, the tonicity can be adjusted by adding a tonicity-adjusting agent to obtain the preferred tonicity. If needed, the viscosity can be adjusted by a viscosity-modifying agent to obtain the preferred viscosity. The final acidity can be adjusted by adjusting the concentrations of the buffering agents or by adding an acid or a base.

The solution formulations were prepared by adding the excipients, one at a time to an appropriate amount of water, followed by mixing until dissolved. Once all excipients had been added and dissolved, norketotifen was added to the solution of excipients and mixed continuously until dissolved. The acidity of the solutions was measured and adjusted by modifying the buffer system or by adding an acid or a base solution to the desired pH. If needed, viscosity and tonicity were adjusted as indicated above.

Example 2

Ophthalmic Ointments and Gels

An example of a preferred composition for a topical hydrophilic ophthalmic gel containing norketotifen hydrogen fumarate (HF) is shown in Table 2.

Preferred ophthalmic hydrophilic ointments or gels containing norketotifen may contain excipients at concentrations that are different from those shown in Table 2. Ophthalmic hydrophilic ointments or gels containing norketotifen may contain excipients that are different from those shown in Table 2.

Topical hydrophilic ophthalmic gel and ointment compositions containing norketotifen can keep the drug in the eye for an extended period of time and the prolonged exposure will enhance drug delivery.

Ophthalmic hydrophilic ointments and gels were made, comprising norketotifen at concentrations that were usually between 0.010 percent and 1.0 percent (w/w, calculated as free base), although such formulations may contain in excess of 5.0 percent of norketotifen. Said hydrophilic ointment and gel formulations have a viscosity that ranged from 5,000 to 500,000 cP, preferably from 20,000 to 200,000 cP. Examples of thickeners/gelling agents, used in the present studies, are polyethylene glycol 300 and/or polyethylene glycol 3350 and/or polyethylene sorbate (polysorbate) and/or chitosan. A compatible surfactant, such as poloxamer 407 can also be added, preferably in a concentration less than 25 percent, more preferred in a concentration less than 20 percent by weight. It was also found that ophthalmic hydrophilic ointments and gels, containing norketotifen, could also contain selected excipients, such as humectants such as for example sorbitol, viscosity modifying agents such as for example methyl cellulose, tonicity agents such as for example NaCl or propylene glycol, chelating agents such as for example edetate or polysaccharides, buffers such as for example phosphate buffers, surfactants such as for example glyceryl stearate, mucoadhesives such as for example polyisobutylcyanoacrylate, antioxidants such as for example BHA or BHT and preservatives such as for example BAK or PHMB. Suggested concentrations of these excipients are as shown previously in this document.

Said gels and ophthalmic hydrophilic ointments were designed for once-daily ocular administration or for repeated administrations from two to five times daily. The terms "gel" and "ointment" are used interchangeably.

The selected hydrophilic ointment/gel in Table 2 is thick but miscible with water. This composition can hold the drug product in the eye of the patient for an extended time, which will enhance drug delivery.

TABLE 2

An example of a preferred topical hydrophilic ophthalmic ointment or gel containing norketotifen.

|  | Batch OG1009 |
|---|---|
| Norketotifen hydrogen fumarate (%) | 0.208 (1) |
| or Norketotifen free base (%) | 0.150 |
| PEG 300 (%) if norketotifen HF is used | 69.790 |
| PEG 300 (%) if norketotifen FB is used | 69.850 |
| PEG 3350 (%) | 30.000 |

(1) Equivalent to 0.15 percent of norketotifen free base (FB)

Batch OG1009 used a mixture of the polyethylene glycols PEG 300 and PEG 3350 as solvent for norketotifen.

The composition of Table 2 was prepared by adding the two polyethylene glycols to a suitable container and heating to 60-65° C. This heating step melts the high molecular weight polyethyleneglycol. Next, norketotifen was added and the composition was mixed until the active ingredient was dissolved. Finally, the composition was cooled with mixing to allow the ointment/gel to thicken. The viscosity was 30,000 cP or greater. The pH range for these compositions was not measured since the formulations were non-aqueous. If needed, the tonicity can be adjusted by adding a tonicity-adjusting agent to obtain the preferred tonicity. If needed, a preservative can be added. The concentration of norketotifen HF can be from about 0.001% to about 0.15% by weight if dissolved in PEG 300 and from about 0.001% to about 0.25% in a mixture of PEG 300 and PEG 3350.

Example 3

Ophthalmic Hydrophobic Ointments

An example of preferred compositions for topical hydrophobic ophthalmic ointments containing norketotifen hydrogen fumarate (HF) is shown in Table 3.

Preferred hydrophobic ophthalmic ointments containing norketotifen may contain excipients at concentrations that are different from those shown in Table 3. Hydrophobic ophthalmic ointments containing norketotifen may contain excipients that are different from those shown in Table 3.

The tested hydrophobic ointments were not miscible with water. These compositions can hold the drug product in the eye of the patient for an extended time and will enhance drug delivery.

Ophthalmic hydrophobic ointments and gels may contain norketotifen at concentrations between 0.001 percent and 5.0 percent, more preferably between 0.01 percent and 1.0 percent. Said ophthalmic hydrophobic ointments and gel solutions were having viscosity in the range of range from 5,000 to 500,000 cP and preferably from 20,000 to 200,000 cP. Said ophthalmic hydrophobic ointments and gels have tonicity between 150 and 450 mOsm, preferably between 230 and 330 mOsm. Said ophthalmic hydrophobic ointments and gels can also contain other excipients, such as humectants, viscosity modifying agents, tonicity agents, chelating agents, buffers, surfactants, mucoadhesives, antioxidants and preservatives. Said ophthalmic hydrophobic ointments and gels were designed for once-daily ocular administration or for repeated ocular administrations from two to five times daily to a mammal in need thereof.

TABLE 3

An example of a preferred hydrophobic ointments containing norketotifen HF.

|  | Batch HO1012 |
|---|---|
| Norketotifen HF (%) | 0.0346 (1) |
| Propylene glycol (%) | 2.500 |
| Glyceryl stearate (%) | 0.500 |
| Cetyl alcohol (%) | 0.500 |
| White petrolatum | q.s. (2) |

(1) Equivalent to 0.025 percent w/w as free base.
(2) quantum sufficit

Batch HO1012 contained propylene glycol as a solvent for norketotifen, glycerol stearate and cetyl alcohol as surfactants and white petrolatum as base.

The hydrophobic ointment was prepared by dissolving norketotifen in propylene glycol. Next, glyceryl stearate, cetyl alcohol, and white petrolatum were added to a suitable container and heated to 65-70° C. This heating step melts the surfactants and the petrolatum. Next, norketotifen solution was slowly added and the composition mixed until the solvent was dispersed. Finally, the composition was cooled with mixing to allow the ointment to thicken.

If needed, acidity can be adjusted by adding an acid solution or a base solution to obtain the preferred acidity. If needed, tonicity can be adjusted by adding a tonicity-adjusting agent to obtain the preferred tonicity. If needed, viscosity can be adjusted by a viscosity-modifying agent to obtain the preferred viscosity. If needed, a preservative can be added.

Example 4

Ophthalmic Emulsions

Two examples of preferred compositions for topical ophthalmic emulsions containing norketotifen hydrogen fumarate (HF) are shown in Table 4 below (E1012 and E1015). Batches E1112 and E1115 were identical to E1012 and E1015, but were without the preservatives.

Topical ophthalmic emulsions containing norketotifen may contain excipients that are different from those shown in the examples in Table 4.

Ophthalmic emulsions were made, comprising norketotifen at concentrations between 0.01 percent and 5.0 percent, preferably between 0.01 percent and 1.0 percent. Said ophthalmic emulsions were having a viscosity in the range from 1.0 to 300,000 cP and preferably from 2.0 to 90,000 cP and most preferred from 2.5 to 75,000 cP. Said ophthalmic emulsions had osmolality between 150 and 450 mOsm and most preferably between 230 and 330 mOsm. Said ophthalmic emulsions had pH of 4 to 7, preferably pH 5.2 to 6.2. Said ophthalmic emulsions could also contain excipients, such as humectants, viscosity modifying agents, tonicity agents, chelating agents, buffers, surfactants, mucoadhesives, antioxidants and preservatives.

TABLE 4

Examples of preferred ophthalmic emulsions containing norketotifen. All composition values are concentrations in percent w/w.

| Excipients in percent | E1012 | E1015 | E1112 | E1115 |
|---|---|---|---|---|
| Norketotifen HF (%) | 0.208 (1) | 0.208 (1) | 0.208 (1) | 0.208 (1) |
| Sodium phosphate dibasic | 0.160 | 0.160 | 0.160 | 0.160 |
| Propylene glycol | 1.850 | 1.850 | 1.850 | 1.850 |
| Methylparaben | 0.050 | 0.050 | — | — |
| Propylparaben | 0.010 | 0.010 | — | — |
| Castor oil | 1.250 | 1.250 | 1.250 | 1.250 |
| Polyoxyl 35 castor oil | 1.000 | 1.000 | 1.000 | 1.000 |
| Methylcellulose | 0.200 | — | 0.200 | — |
| 1.0 N HCl or 1.0 N NaOH | q.s. to target pH | q.s. to target pH | q.s. to target pH | q.s. to target pH |
| Water | q.s. (2) | q.s. (2) | q.s. (2) | q.s. (2) |
| pH | 5.5 | 5.5 | 5.5 | 5.5 |

(1) Equivalent to 0.15 percent as free base;
(2) quantum sufficit

The batches E1012 and E1015 contained a phosphate buffer, propylene glycol as solvent/moisturizer/tonicity modifier, parabens as preservatives, castor oil and polyoxyl castor oil as surfactants and methylcellulose (if used) as a stabilizer/viscosity modifier. Batches E1112 and E1115 were identical to E1012 and E1015, but were without the preservatives. Several experiments were done and acidity was adjusted over a wide range. It was determined that emulsions can be used at pH of about 5.0 to about 7.0; the preferred acidity is pH 5.5 to pH 6.0.

The selected emulsions in Table 4 were prepared by adding propylene glycol, parabens (if used), castor oil, ethoxylated castor oil, and water to a suitable container. The contents of the container were sonicated with a 1/2" ultrasonic probe (Sonics Inc. Vibra Cell) for 20 minutes. The resulting emulsion droplets were mostly less than 0.5 microns. The emulsion was filtered through a 0.22-micron cellulose acetate filter. After filtration, norketotifen, buffer salt, and polymer (if used) were added.

If needed, the tonicity can be adjusted by adding a tonicity-adjusting agent to obtain the preferred tonicity. The viscosity of norketotifen emulsions can be adjusted by a compatible viscosity-modifying agent in an amount that is needed to obtain the preferred viscosity.

Example 5

Ophthalmic Liposome Compositions

An example of a preferred ophthalmic liposome composition containing norketotifen hydrogen fumarate (HF) is shown in table 5. Preferred ophthalmic liposome compositions containing norketotifen may contain excipients of concentrations that are different from those shown in Table 5. Ophthalmic liposome compositions containing norketotifen may contain excipients that are different from those shown in Table 5.

Ophthalmic liposome compositions were made, comprising norketotifen at concentrations preferably between 0.01 percent and 0.50 percent. Said ophthalmic liposome compositions were having a preferred viscosity that ranged from 1.0 to 100,000 cP and more preferably from 2.0 to 90,000 cP. Said ophthalmic liposome compositions were having an osmolality between 150 and 450 mOsm, preferably between 230 and 330 mOsm. Ophthalmic liposome compositions have pH of 4 to 7, preferably pH 5.2 to 6.2. The liposome compositions are approximately iso-osmotic. Said ophthalmic emulsions also contained excipients, such as humectants, viscosity modifying agents, tonicity agents, chelating agents, buffers, surfactants, muco-adhesives, antioxidants and preservatives. Said ophthalmic emulsions were designed for once-daily ocular administration or for repeated ocular administrations from two to five times daily to a mammal in need thereof.

Incorporating norketotifen in a selected liposome composition will enhance residence time in the eye and improve ocular drug delivery to the tissues. A preferred liposome composition containing norketotifen is shown in Table 5 below. The acidity can be changed by adjustment of the buffer or by adding an acid or a base as know as known to those skilled in the art.

TABLE 5

Example of a preferred ophthalmic liposome composition containing norketotifen HF.

| Excipients in percent | LIP1011 |
| --- | --- |
| Norketotifen HF (%) | 0.208 (1) |
| Sodium phosphate dibasic | 0.160 |
| Glycerin | 2.400 |
| Benzalkonium chloride | 0.010 |
| Soy lecithin | 1.000 |
| Cholesterol | 0.050 |
| Water | q.s. (2) |
| 1.0 N HCl | q.s. to target pH |
| pH | 4.6 to 6.2 |

(1) Equivalent to 0.15 percent w/w as free base;
(2) quantum sufficit
pH is 4.6 to 6.2, preferably about 5.5.

Batch LIP1011 contained dibasic sodium phosphate as a phosphate buffer, glycerin as a moisturizer/tonicity modifier, benzalkonium chloride as a preservative and soy lecithin and cholesterol as surfactants. Several experiments were done and acidity was adjusted over a wide range. It was determined that emulsions can be used at an acidity from about pH 5.0 to about pH 7.0; the preferred acidity is pH 4.6 to pH 6.2; most preferred is pH 5.5.

To prepare liposome compositions containing norketotifen, lecithin and cholesterol were dissolved in ethanol and added to a suitable container. Ethanol was evaporated leaving behind a lipid film. The remaining components of the composition were dissolved in water and this solution was added to the lipids to form a coarse dispersion of vesicles. This dispersion was sonicated with a ½" ultrasonic probe (Sonics Inc. Vibra Cell) for 15 minutes. The resulting liposomes were mostly less than 0.5 microns. The liposome composition was filtered through a 0.22-micron cellulose acetate filter.

If needed, the tonicity can be adjusted by adding a tonicity-adjusting agent to obtain the preferred tonicity. If needed, the viscosity can be adjusted by a viscosity-modifying agent to obtain the preferred viscosity.

Example 6

Ophthalmic Solutions of Norketotifen Free Base

Ophthalmic compositions containing norketotifen free base may contain excipients that are different from those shown in Tables 1A, 1B or 7.

Compositions containing solutions of norketotifen FB represent a challenge due to the low water solubility of the free base. It has now been found that norketotifen FB can be dissolved in propylene glycol, glycerin, ethanol and isopropyl alcohol. Surfactants, such as for example polysorbate 80, polysorbate 20, poloxamer 407, poloxamer 188, polyoxyl 40 stearate or sorbitan monolaurate can also be used to dissolve norketotifen FB. Liposomes, as for example those made with phospholipids can also be used with the free base of norketotifen. Norketotifen FB can also be formulated as a suspension and other formulations of the present invention. Several experiments were done and acidity was adjusted over a wide range. It was determined that emulsions can be used at pH of about 5.0 to about 7.0; the preferred acidity is pH 5.5. An example of a preferred suspension containing norketotifen free base is shown in Table 6, below, where all percent are w/w.

TABLE 6

An example of a preferred ophthalmic suspension, containing norketotifen free base (FB).

| | SUS1011 |
| --- | --- |
| Norketotifen FB (%) | 0.20 |
| Poloxamer 407 (%) | 0.2 |
| Boric acid (%) | 0.1 |
| Sodium chloride (%) | 0.09 |
| HCl/NaOH for pH adjustment | As needed |
| Water | q.s. (1) |
| pH | 5.5 |

(1) quantum sufficit

If needed, the tonicity can be adjusted by adding a tonicity-adjusting agent to obtain the preferred tonicity. If needed, the viscosity can be adjusted by a viscosity-modifying agent to obtain the preferred viscosity. If needed, a preservative, such as for example BAK may be added in concentrations shown previously in this document.

Example 7

Ocular Minitablets

Use of Ocular Mucoadhesive Minitablets and Gel-Forming Minitablets
Mucoadhesive Ocular Minitablets Norketotifen ocular minitablets, using pregelatinized starch, hydroxypropylcellulose and Avicel and containing 5 percent Carbopol as the bioadhesive polymer (to reduce the risk for expulsion) and one or more water-insoluble polymers, such as ethylcellulose, unmodified or thiolated polyacrylic acid are prepared by compression. Minitablets are placed under the eyelid of rabbits. The effects on tear-film stability are examined using fluorescein staining after single dosing. Preliminary results indicate that inserts containing thiolated polyacrylic acid offer prolonged fluorescein concentration on the eye.

Gel-Forming Ocular Minitablets

Gel-forming ocular minitablets made of thiomers may also be used as an ocular dosage form for norketotifen.

Example 8

Ocular Irritation Test

Tests of Ocular Irritation of Norketotifen in Various Formulations.

Methods

New Zealand White rabbits, weighing 2 to 4 kilograms were used. Test formulation, in volumes of 0.1 ml were instilled into the conjunctival sac of six rabbit eyes of groups. Said volume of each formulation was repeatedly instilled every 30 minutes for 3 hours (a total of seven instillation into the eyes of rabbits. Ocular irritation was scored according to both Draize et al., 1944 and Kay and Calandra, 1962. Scorings were performed before each instillation and 30 minutes, 3 hours and 24 hours after the last instillation.

The formulations of norketotifen in Table 7 were prepared and tested and the results were compared with irritation by norketotifen in excipient-free solutions. Table 7 indicates that the solutions of norketotifen HF were 0.276% since the solubility of norketotifen hydrogen fumarate (HF) in some or all of these solutions may have been less than 0.276 percent. In the present study, norketotifen HF was dissolved to an intended concentration of 0.276 percent in the various solutions, using stirring and over-night sonication at room temperature. After sonication, all solutions were filtered through a 0.45 μm non-pyrogenic MILLEX® HV filter unit before being used for ocular tests. Thus, all of the solutions used for the ocular irritation tests in Table 7 contained the highest possible concentrations of norketotifen HF.

TABLE 7

Formulations used for ocular irritation tests

| Ingredients | Formulation A | Formulation B | Formulation C | Formulation D |
|---|---|---|---|---|
| Norketotifen HF (*) | ≤0.276% | ≤0.276% | ≤0.276% | ≤0.276% |
| Sodium phosphate dibasic | 0.473% | — | — | — |
| Sodium phosphate monobasic, monohydrate | 0.460% | — | — | — |
| Sodium Chloride | 0.480% | — | — | — |
| Benzalkonium chloride (BAK) | 0.010% | — | 0.010% | — |
| Sodium citrate | — | 0.300% | — | — |
| Propylene glycol | — | 1.750% | — | — |
| Methylparaben | — | 0.030% | — | — |
| Propylparaben | — | 0.010% | — | — |
| EDTA | — | — | 0.100% | 0.100% |
| Boric Acid | — | — | 0.095% | 0.095% |
| Sorbitol | — | — | 4.6% | 4.6% |
| Water | q.s. | q.s. | q.s. | q.s. |
| pH | 5.5 | 5.5 | 5.5 | 5.5 |

(*) 0.276% norketotifen HF = 0.20% norketotifen FB.

Solutions of norketotifen were similarly prepared in excipient-free solutions containing only norketotifen HF 0.0345 percent by weight, dissolved in water or in saline, and filtered as described above. The excipient-free solutions containing norketotifen HF were tested by ocular instillations in one eye of 6 rabbits, followed by repeated Draize scorings and Kay & Calandra scorings as described above.

Results

The irritation scoring demonstrated that excipient-free norketotifen HF, even at the low concentration of 0.0345% caused irritation after instillations into rabbit eyes. No ocular irritation by norketotifen was observed when norketotifen in the highest possible concentration (≤0.276%) was administered in either of the Formulations A, B, C, or D.

Conclusions

It was surprisingly found that even in the highest concentrations possible, and even after seven consecutive instillations into the eye, norketotifen was not causing any ocular irritation, when administered in the preferred formulations, herein represented by Formulations A, B, C and D. These results were contrary to results obtained with excipient-free solutions.

Example 9

Antimicrobial Effectiveness Testing

Preservative Challenge Tests of New Formulations

Ocular products in multidose containers must be adequately preserved to prevent contamination during repeated use. The most commonly used preservative, benzalkonium chloride (BAK) has known side effects on the eye (Baudouin, 2008) and efforts are made to decrease the concentration of BAK (Table 1A: LOBAK formulations) or completely eliminate BAK (Table 1A: NOBAK formulations).
Method Preservative challenge tests, slightly modified after U.S. Pharmacopeia 51 Antimicrobial Effectiveness Testing, were performed. USP (51) is a standard test used to determine the effectiveness of antimicrobial substances in ophthalmic products. The present tests were using 150 ml of each formulation and covered five organisms: *Escherichia coli* (fermentative G−), *Pseudomonas aeruginosa* (non-fermentative G−), *Staphylococcus aureus* (G+), *Aspergillus niger* (fungus) and *Candida albicans* (yeast).

The number of inoculated cells was $0.5 \times 10^5$ per mL and the incubation temperature was 25° C. (rt) for all inoculations. Plating for measuring of recoveries were performed weekly over 4 weeks. If the numbers of cell colonies remained constant or were declining for all five microorganisms, the norketotifen formulation was defined as having self-preserving qualities; if the numbers of colonies increased for any of the five microorganisms, the formulations were not considered as having self-preserving activity.

Tests were performed at pH 4.0, 4.5, pH 5.0 and pH 6.0 and with formulations containing 0.208 percent norketotifen HF. All formulations referred to here were devoid of preservatives and contained: EDTA 0.1%; Boric acid 0.095%; Sorbitol 4.6% and water q.s. (see Table 1A: NOBAK formulations).
Results The antimicrobial activity of the norketotifen formulations was pH-dependent. When tested at pH 5 and pH 6, preferred formulations containing 0.208 percent or 0.0345 percent norketotifen HF were surprisingly found to be self-preserving. Thus, the numbers of colonies of all five microorganisms declined or stayed the same during the course of the 4-week tests in formulation with pH ≥5.0.

TABLE 8

Results from preservative challenge tests of formulations containing norketotifen 0.0345 percent (NOBAK formulation; Table 1A).

| FORMULATION | pH 4.0 | pH 4.5 | pH 5.0 | pH 6.0 |
|---|---|---|---|---|
| NOBAK | *** | **** | ***** | ***** |

\*\*\* indicate that for three of the five microorganisms the numbers of colonies declined or remained constant (the formulation did not pass the test).
\*\*\*\* indicate that for four of the five microorganisms the numbers of colonies declined or remained constant (the formulation did not pass the test).
\*\*\*\*\* indicate that for all five microorganisms the numbers of colonies declined or remained constant (the formulation passed the test).

Conclusion

Ocular formulations of norketotifen according to the present invention can be used without preservatives in formulation with pH ≥5.0.

Example 10

Solubility of Norketotifen

The norketotifen hydrogen fumarate salt and other acceptable salt forms, such as for example the hydrochloride salt are acid salts of a weak base. As such the salts can be expected to have fairly constant solubility over a wide pH range. Formulations that contain an excipient or a combination of excipients that decrease the solubility of the active ingredient may not be useful.
Method Saturated solutions of norketotifen were prepared at room temperature by stirring, overnight sonication and filtering of the saturated supernatant solutions. An HPLC method for the determination of concentrations of norketotifen was developed:

| Column | XTerra RP-$C_{18}$ (4.6 × 150 mm, 5 mm) |
|---|---|
| Detection | UV at 300 nm |
| Mobile phase | A: 10% ACN/90% $H_2O$, 0.1% TFA |
| | B: 90% t ACN/10% $H_2O$, 0.1% TFA |
| Gradient | 0.0 min.: 100% A; 15.0 min.: 100% B; |
| | 15.5 min.: 100% A. Run time: 25 min |
| Flow rate | 1 mL |
| Column Temp. | 30° C. |
| Sample conc. | 0.025 to 0.1 mg/mL |
| Injection volume | 20 mL |

ACN = acetonitrile
TFA = trifluoroacetic acid

The HPLC system was a HP 1050 with a variable wavelength detector. Over a range of 0.025 to 0.1 mg/mL, the assay showed good linearity with a correlation coefficient greater than 0.999. The relative standard deviation was approximately 0.3 percent for the main peak area.

The HPLC assay described here was also used for determination of concentrations of norketotifen in the compositions of the present invention. Prior to analysis, norketotifen was extracted from the ophthalmic compositions, using standard methods, well known to those skilled in analytical chemistry.
Results The solubility of norketotifen at pH 4.0 was found to be 2.16 mg/ml in (unbuffered) water and the solubility remained approximately the same as pH was increased (by adding NaOH) to pH 5.0, pH 6.0 and pH 7.0. The water solubility of norketotifen was decreased to 2.10 mg/ml at pH 8.6. The water solubility of norketotifen was sharply decreased at higher pH and at pH 8.75 the solubility of norketotifen was decreased to approximately 1.0 mg/ml.

In the preferred solution formulations NOBAK, LOBAK, MIDBAK, HIBAK, PHMB, S1008, S1009 and S1010 (Tables 1A and 1B), the solubility of norketotifen was from about 2.4 mg/ml to about 2.7 mg/ml (pH 5.5), representing an improved solubility when compared with solubility in water.

The solubility of norketotifen was significantly increased in certain formulations, such as gels and ointments where solvents were not water. Thus, the solubility of norketotifen was about 10 mg/ml in formulation OG1009 (Table 2), where the solvent was a mixture of two polyethylene glycols.

Example 11

Stability of Norketotifen Formulations

Stability of norketotifen formulations was studied after incubation at various temperatures, acidity and time intervals.
Methods The concentrations of norketotifen were measured after incubation periods of various lengths.
Results Examples of test results are shown Table 9. All concentrations of norketotifen are mg/ml.

TABLE 9A

Stability of a formulation containing benzalkonium chloride. Formulation (See Table 1A): LOBAK; pH 5.5. Concentrations are in mg/ml.

| Temperature | Week 1 | Week 2 | Week 3 | Week 4 |
|---|---|---|---|---|
| 5° C. | 0.3454 | 0.3438 | 0.3423 | 0.3442 |
| 25° C. | 0.3453 | 0.3424 | 0.3439 | 0.3426 |
| 40° C. | 0.3453 | 0.3425 | 0.3437 | 0.3444 |
| 55° C. | 0.3430 | 0.3391 | 0.3449 | 0.3462 |

TABLE 9B

Stability of a norketotifen formulation without benzalkonium chloride. Formulation (See Table 1A): NOBAK; pH 5.5. Concentrations are in mg/ml.

| Temperature | Week 1 | Week 2 | Week 3 | Week 4 |
|---|---|---|---|---|
| 5° C. | 0.3429 | 0.3421 | 0.3432 | 0.3442 |
| 25° C. | 0.3436 | 0.3426 | 0.3426 | 0.3438 |
| 40° C. | 0.3429 | 0.3419 | 0.3435 | 0.3457 |
| 55° C. | 0.3412 | 0.3416 | 0.3400 | 0.3440 |

TABLE 9C

Stability of a norketotifen formulation without benzalkonium chloride. Formulation (See Table 1A): NOBAK; pH 6.5. Concentrations are in mg/ml.

| Temperature | Week 1 | Week 2 | Week 3 | Week 4 |
|---|---|---|---|---|
| 5° C. | 0.3436 | 0.3409 | 0.3429 | 0.3422 |
| 25° C. | 0.3417 | 0.3400 | 0.3408 | 0.3433 |
| 40° C. | 0.3397 | 0.3375 | 0.3383 | 0.3371 |
| 55° C. | 0.3199 | 0.3075 | 0.3014 | 0.2853 |

Conclusions

It can be concluded from Tables 9A and 9B that the formulations LOBAK and NOBAK at pH 5.5 are stable over a prolonged period as substantiated by the results from the accelerated stability tests at 40° C. and 55° C.

Table 9C demonstrates that norketotifen is not stable in solution formulations of pH 6.5 under conditions of accelerated testing (55° C.).

Example 12

Antihistaminic Activity

Antihistaminic (H-1) Activity In Vivo after Oral Administrations to Rats.

Methods

Male rats (150-200 g) were starved overnight and twelve hours after dorsal depilation, the animals were dosed orally with the test compound(s). Four dorsal test areas were marked with permanent ink. Exactly 60 min after the dosing of the test compound, two intradermal injections of histamine (50 microliter; 1.0 mg/ml of histamine di-HCl) were performed, one on each side on the back of the animal. Two intradermal injections of the vehicle for the histamine solution were also performed. Evans blue dye (20 mg/kg) was injected iv 1 minute prior to the intra-dermal injections of histamine and the histamine vehicle. Twenty minutes were allowed for the wheal response to fully develop, whereupon the animals were euthanized and the dorsal skin containing the intradermal wheals was deflected. The blue spotted areas were measured in square millimeters and the duplicate vehicle wheal responses were averaged. In vehicle-treated animals, the wheal area, on average, was increased by histamine by 98 mm². The inhibition was calculated in percent difference from the corresponding vehicle baseline value.

Results

TABLE 10

Antihistaminic activity in vivo after oral administration.

| Test compound/ Dose (mg/kg) | Histamine (mm²) | Saline (mm²) | Histamine effect (mm²) | Inhibition (percent) |
|---|---|---|---|---|
| Vehicle* | 122 ± 9 | 24 ± 2 | 98 | — |
| Vehicle** | 107 ± 4 | 25 ± 1 | 82 | — |
| Ketotifen; 1 | 68 ± 6 | 21 ± 2 | 47 | 43 |
| Ketotifen; 10 | 24 ± 2 | 22 ± 3 | 2 | 97 |
| Norketotifen; 1 | 114 ± 8 | 22 ± 1 | 92 | 6 |
| Norketotifen; 10 | 39 ± 2 | 22 ± 1 | 17 | 83 |
| Norketotifen; 50 | 10 ± 1 | 12 ± 1 | 0 | 100 |
| DPH; 10*** | | | | 31 |

*Vehicle for norketotifen.
**Vehicle for ketotifen.
***DPH = diphenhydramine (generic)

Both ketotifen and norketotifen are potent antihistaminic compounds. The dose/response curves for ketotifen and norketotifen were not parallel. Ketotifen was approximately twice as potent as norketotifen as an antihistamine at dose levels offering 75% inhibition of the histamine effect ($IC_{75}$). Both ketotifen and norketotifen were more potent than the reference compound (diphenhydramine).

Conclusions

As an antihistamine, ketotifen was more potent than norketotifen and both compounds were more potent than diphenhydramine (Benadryl®). It is also concluded that norketotifen was well absorbed in rats after oral administration.

Example 13

Inhibition of Granulocyte Activation

Anti-inflammatory activity was measured as effects on granulocyte activation ("mast cell stabilization").

Methods

In the present studies, effects on granulocyte activation was studied as inhibition of histamine release from human granulocytes (buffy coat) by norketotifen. The method is a modification of the method described by Nolte, H. et al., 1988. Granulocytes were obtained from human volunteers and mediator release was induced by incubation (20 min/37° C.) with the calcium ionophore A23187 (5 μM) in the presence or absence of a test article. Histamine was selected as an indicator for mediator release because of the ease with which histamine can be analyzed, using commercially available kits. The test articles were evaluated, in duplicate, at five concentrations and IC50-values were calculated.

The calcium ionophore A23187 was used to increase intracellular calcium concentration of the granulocytes. Those skilled in the art of pharmacology realize that the presently used A23187-method mimics in vivo activation, initiated by IgE- and cAMP-induced increase of the intracellular calcium concentration, which in turn triggers a release of inflammatory mediators (such as histamine) from intracellular granulae, which is a process that is usually referred to as granulocyte "activation." The concentrations of norketotifen and ketotifen used here had to be relatively high, since the validated method for in vitro granulocyte activation uses high concentrations, high temperatures and a relatively long exposure time for the calcium ionophore.

Results

Norketotifen (IC50=9.2 μM) was approximately 10 times more active than ketotifen (IC50=91 μM) in inhibiting A23187-induced granulocyte activation.

TABLE 11

Inhibition of histamine release (IC50).

| Test Article | IC50 (μM) |
|---|---|
| RS-ketotifen | 91 |
| RS-norketotifen | 9.2 |

Conclusion

It is concluded that norketotifen was about ten times more potent than ketotifen as an inhibitor of human granulocyte activation, which is an anti-inflammatory effect.

Combinations

Ophthalmic compositions of norketotifen may contain one or more additional, therapeutically active ingredients. In addition to norketotifen, such combination compositions may contain one or more anti-inflammatory drug, such as for example a steroid belonging to the class consisting of corticosteroids, such as for example rimexolone (Vexol®, Alcon), fluorometholone (generic), prednisolone acetate (generic), loteprednol etabonate (generic), dexamethasone (generic) and difluprednate (Durezol™, Sirion), or an NSAID, such as for example nepafenac (Nevanac™, Alcon), diclofenac (Voltaren™, Novartis), ketorolac (Acular™, Allergan), bromfenac (Xibrom™, Ista), ibuprofen (generic) and indomethacin (generic).

In addition to norketotifen, such combination compositions may contain one or more immunosuppressants, such as cyclosporine (generic), tacrolimus (Protopic™, Fujisawa) and pimecrolimus (Elidel®, Novartis).

In addition to norketotifen, such combination compositions may contain one or more antimicrobial agents, such as for example aminoglycosides (e.g. neomycin), quinolones (e.g. ofloxacin), macrolides (e.g. azithromycin), polypeptides (e.g. bacitracin), sulfonamides (e.g. sulfacetamide), or combination products (e.g. polymyxin B).

All combination products using compositions described herein are included in the present invention.

Equivalents

Norketotifen can also be dissolved and administered in an oil-base composition or norketotifen can be dissolved in the oil phase of an oil-in-water emulsion system, which confers certain advantages to the patient, such as higher drug concentrations, minimal decomposition of norketotifen by hydrolysis, and lubrication and improved comfort to the eye.

Norketotifen can also be administered via the nasal route, the oral route or various parenteral routes using compositions described herein and devices known to those skilled in the art. Regular or controlled release tablets or capsules contain from 1 mg to 20 mg norketotifen. Combinations of routes, such as for example oral doses combined with topical ocular doses may have advantages, as known to those skilled in the art of drug formulations.

Micronized norketotifen can be used in ocular compositions of norketotifen and have particle sizes where >90 percent of the material is <10 microns. Also nanoparticles of norketotifen can be used in ocular compositions thereof and have particle sizes where >90 percent of the material is <1 micron.

It may be necessary to adjust the formulations, shown in the examples herein in order to make said formulations autoclavable. Autoclavable ocular formulations are well known and have been described for example in U.S. Pat. No. 6,776,982 that is hereby incorporated by reference. Autoclavable compositions of norketotifen are included in the present invention.

Norketotifen has now been found to be a potent wound healing modulator and can be used to facilitate ocular surface re-epithelization and to prevent corneal haze resulting from scar formation due to inflammation. Similar effects have previously been described for ketotifen and cyproheptadine (U.S. Pat. No. 5,624,893) and olopatadine (U.S. patent Ser. No. 11/947,041). The formulations of norketotifen described herein are suitable vehicles for the delivery of norketotifen to the eyes of patients in need of a wound healing modulator. Norketotifen HF solutions may contain concentrations containing about 0.02% to 0.21% norketotifen. Solutions containing solubilizers may have higher concentrations of norketotifen. Likewise, emulsions, gels, ointment, suspensions and similar formulation may contain concentrations of up to 4%. All equivalents are included in the present invention.

What is claimed is:

1. A method of treating a patient suffering from xerophthalmia, comprising topical administration to the eye of said patient in need thereof an ophthalmic formulation, acceptable to the eye, free from any added preservative, and containing a solution of norketotifen or a pharmaceutically acceptable salt thereof in a concentration of 0.001 percent to 0.3 percent by weight, wherein the solution has a pH of ≥4.5.

2. The method of claim 1, wherein said patient is a member selected from the group consisting of humans, dogs and cats.

3. The method of claim 1, wherein the formulation exhibits constant or declining numbers of cell colonies after up to 4 weeks of incubation at 25° C. with 0.5×10⁵ cells per mL of four out of five of the following microorganisms: *Escherichia coli, Pseudomonas aeruginosa, Staphylococcus aureus, Aspergillus niger* and *Candida albicans*.

4. The method of claim 1, wherein the solution is an aqueous solution.

5. The method of claim 1, wherein the ophthalmic formulation is formulated for use in a multidose container.

6. The method of claim 1, wherein the solution has a pH of ≥about 5.

7. The method of claim 6, wherein the ophthalmic formulation exhibits constant or declining numbers of cell colonies after up to 4 weeks of incubation at 24° C. with 0.5×10⁵ cells per mL of *Escherichia coli, Pseudomonas aeruginosa, Staphylococcus aureus, Aspergillus niger* and *Candida albicans*.

8. The method of claim 1, wherein the ophthalmic formulation further comprises a chelating agent, a stabilizing agent, a buffering agent, or a humectant.

9. The method of claim 5, wherein the formulation further comprises EDTA, boric acid and sorbitol.

* * * * *